United States Patent
Miller et al.

(10) Patent No.: US 11,717,599 B2
(45) Date of Patent: Aug. 8, 2023

(54) BREAST SHIELD FOR A BREAST PUMP SYSTEM

(71) Applicant: Babyation Inc., St Louis, MO (US)

(72) Inventors: Jared Miller, Clayton, MO (US); Samantha Rudolph, Clayton, MO (US); Arthur Deptala, Clayton, MO (US); Corey Feit, Clayton, MO (US)

(73) Assignee: Babyation Inc., St. Louis, MO (US)

( * ) Notice: Subject to any disclaimer, the term of this patent is extended or adjusted under 35 U.S.C. 154(b) by 0 days.

(21) Appl. No.: 16/525,022

(22) Filed: Jul. 29, 2019

(65) Prior Publication Data
US 2019/0365971 A1    Dec. 5, 2019

Related U.S. Application Data (63) Continuation-in-part of application No. 15/149,525, filed on May 9, 2016, now Pat. No. 10,363,347.

(60) Provisional application No. 62/158,303, filed on May 7, 2015.

(51) Int. Cl.
*A61M 1/06* (2006.01)

(52) U.S. Cl.
CPC .............. *A61M 1/06* (2013.01); *A61M 1/064* (2014.02); *A61M 1/066* (2014.02); *A61M 1/06935* (2021.05); *A61M 2205/3337* (2013.01); *A61M 2205/3561* (2013.01); *A61M 2205/3584* (2013.01); *A61M 2205/50* (2013.01); *A61M 2205/7518* (2013.01); *A61M 2205/7545* (2013.01); *A61M 2205/8206* (2013.01)

(58) Field of Classification Search
CPC ........ A61M 1/06; A61M 1/064; A61M 1/066; A61J 13/00
See application file for complete search history.

(56) References Cited

U.S. PATENT DOCUMENTS

| | | |
|---|---|---|
| 603,564 A | 5/1898 | Hoover |
| 3,822,703 A | 7/1974 | Davisson |
| 4,607,596 A | 8/1986 | Foreman |
| 4,680,028 A | 7/1987 | Stuart |
| 4,772,262 A | 9/1988 | Grant et al. |

(Continued)

FOREIGN PATENT DOCUMENTS

WO    WO-2008061589 A2 *  5/2008  ............ A61M 1/007

OTHER PUBLICATIONS

Patent Cooperation Treaty, International Search Report for PCT/us2019/052170, 5 pages dated Feb. 19, 2020.

*Primary Examiner* — Courtney B Fredrickson
(74) *Attorney, Agent, or Firm* — Bryan Cave (57) ABSTRACT

A breast pump system is provided with a suction tubing and a milk tubing, wherein the suction tubing and milk tubing each have first and second ends, and comprise a unitary tube structure. The system includes a first connector that has a first portion for coupling to a breast pump and the suction tubing, and a second portion for coupling to a milk bottle and the milk tubing. The system also includes a second connector that has a first portion coupled to a suction port of a breast shield and the suction tubing, and a second portion coupled to a breast milk collecting port and the milk tubing. A breast shield system with a flexible diaphragm and a cover is provided that may be coupled to the breast pump system. A dual suction path filter cartridge is also provided.

11 Claims, 12 Drawing Sheets

(56) References Cited

U.S. PATENT DOCUMENTS

| | | |
|---|---|---|
| 4,964,851 A | 10/1990 | Larsson |
| 5,295,957 A | 3/1994 | Aida et al. |
| 5,415,632 A | 5/1995 | Samson |
| 5,542,921 A | 8/1996 | Meyers et al. |
| 5,897,580 A | 4/1999 | Silver |
| 5,954,690 A * | 9/1999 | Larsson ............... A61M 1/0068 604/74 |
| 6,004,186 A * | 12/1999 | Penny .................. A61M 1/062 2/104 |
| 6,004,288 A | 12/1999 | Hochstedler |
| 6,213,840 B1 | 4/2001 | Han |
| 6,379,327 B2 | 4/2002 | Lundy |
| 6,383,163 B1 * | 5/2002 | Kelly ..................... A61M 1/06 604/74 |
| 6,383,164 B1 | 5/2002 | Johansen et al. |
| 6,500,143 B2 | 12/2002 | Suh |
| 7,758,540 B2 | 7/2010 | Yamashita et al. |
| 8,118,772 B2 | 2/2012 | Dao et al. |
| 8,137,153 B2 | 3/2012 | Bell |
| 8,398,584 B2 | 3/2013 | Britto |
| 8,500,679 B2 | 8/2013 | Holshouser et al. |
| 8,529,501 B2 | 9/2013 | Wach et al. |
| 8,900,182 B2 | 12/2014 | Britto |
| 10,485,908 B2 * | 11/2019 | Alvarez ................. A61M 1/82 |
| 2001/0044593 A1 | 11/2001 | Lundy |
| 2002/0198489 A1 * | 12/2002 | Silver ................... A61M 1/064 119/14.47 |
| 2003/0191433 A1 | 10/2003 | Prentiss |
| 2004/0127845 A1 | 7/2004 | Renz et al. |
| 2004/0133151 A1 * | 7/2004 | Watanabe ............... A61M 1/06 604/74 |
| 2005/0020971 A1 | 1/2005 | Sung |
| 2005/0043677 A1 | 2/2005 | Kelly et al. |
| 2007/0161330 A1 | 7/2007 | Whitehead |
| 2010/0121267 A1 | 5/2010 | Silver et al. |
| 2011/0071466 A1 | 3/2011 | Wäckerlin |
| 2011/0251552 A1 * | 10/2011 | Brittner .................. A61J 13/00 604/74 |
| 2014/0243766 A1 | 8/2014 | Martuch |
| 2014/0288466 A1 | 9/2014 | Alvarez et al. |
| 2015/0024656 A1 * | 1/2015 | Johnson ................ A61M 1/066 450/36 |
| 2015/0065994 A1 | 3/2015 | Fridman et al. |
| 2015/0196460 A1 | 7/2015 | Brittner |
| 2016/0000980 A1 * | 1/2016 | Alvarez ................. A61M 1/064 604/514 |
| 2016/0325031 A1 | 11/2016 | Miller et al. |
| 2019/0240386 A1 * | 8/2019 | Larsson ................ A61M 1/066 |

\* cited by examiner

BREAST SHIELD FOR A BREAST PUMP SYSTEM

CROSS-REFERENCE TO RELATED APPLICATIONS

This application claims the benefit of provisional patent application 62/158,303 filed May 7, 2015, which is hereby incorporated by reference.

FIELD OF THE INVENTION

The present invention relates to the tubing and connectors used in a breast pump system, where the storage of breast milk and positioning of the pump are remote from the breast.

BACKGROUND OF THE INVENTION

Prior art pump systems are limited to either a knob or up/down buttons for control of the unit. Some systems have dual controls, one for suction and one for speed, but many have just a single control. They typically have either no memory device, or are limited to a single preset setting. Prior art pump systems do not correlate pump settings (suction, cycle time) to amount of milk produced, comfort level, or any other quantifiable values. Prior art systems on the market store the expressed milk in a vessel that is directly connected to the bottom of the breast shield. The means that the user effectively has bottles and multiple tubes hanging from her breasts, which does not allow pumping to be done discreetly. This is extremely awkward for the user. In addition, prior art breast shields are made of hard plastic and are uncomfortable. A further complaint about prior art pumps is that they are noisy and make a pulsed mechanical sound. The larger the pump, the greater the noise created. A further complaint about prior art pumps is that closed system breast shields require many separate components.

SUMMARY OF THE INVENTION

The present invention relates to an improved breast pump system comprising a suction tubing and a milk tubing, wherein the suction tubing and milk tubing each have first and second ends, and wherein the suction and milk tubing are adhered together in a side-by-side manner, to comprise a unitary tube structure. Some embodiments include a first connector that has a first portion for fluid coupling to both a breast pump and the first end of the suction tubing, and a second portion for fluid coupling to both a milk bottle and the first end of the milk tubing. Some embodiments also include a second connector that has a first portion for fluid coupling to both a suction port of a breast shield and the second end of the suction tubing, and a second portion for fluid coupling to both a breast milk collecting port of the breast shield and the second end of the milk tubing. In some embodiments, the first connector is configured to fluidly couple to the breast pump through a suction filter. In some embodiments, the second connector comprises one or more vent holes in the first portion for controlling suction and a diaphragm.

Embodiments of a breast shield system are also provided, which comprises a flexible soft diaphragm having a milk collection port and an outer lip, and a cover portion having an edge, a suction port and an interface, wherein the edge of the cover sealingly couples to the lip of the soft diaphragm. This arrangement of components provides a compact breast shield with a minimum number of parts to clean. The soft diaphragm presents a comfortable seal to the user's body while also providing closed system protection in a single part or in some embodiments, two parts. In some embodiments, the breast shield system comprises a bra pad conforming in shape to the breast shield system, wherein the bra pad can be inserted into a bra to secure and hide the breast shield system. In some embodiments, the suction port is configured for fluid coupling to a suction portion of a connector, and wherein the milk collecting port is also configured for fluid coupling to a milk collection portion of a connector; wherein the suction portion and milk collection portions of the connector are separated.

In some embodiments, the breast pump system further comprises a filter cartridge system coupled. The filter cartridge system comprises a first internal suction path, a second internal suction path, a first set of vent holes that couple to the first internal suction path, a second set of vent holes that couple to the second internal suction path, a first filter element to minimize bacteria from contaminating first filter path, and a second filter element to minimize liquid ingress into the second internal suction path.

In some embodiments, the filter cartridge system further comprises a first open alignment position in which the first set of vent holes is aligned with the first internal suction path and the second set of vent holes is aligned with the second internal suction path. In other embodiments, the filter cartridge system further comprises a second semi-closed alignment position in which the first set of vent holes is aligned with the first internal suction path and the second set of vent holes is out of alignment with the second internal suction path. In some embodiments, the filter cartridge system additionally comprises comprising a third closed alignment position in which the first set of vent holes is out of alignment with the first internal suction path and the second set of vent holes is out of alignment with the second internal suction path.

BRIEF DESCRIPTION OF THE DRAWINGS

The present invention will become more fully understood from the detailed description and the accompanying drawings, wherein.

For simplicity and clarity of illustration, the drawing figures illustrate the general manner of construction, and descriptions and details of well-known features and techniques may be omitted to avoid unnecessarily obscuring the present disclosure. Additionally, elements in the drawing figures are not necessarily drawn to scale. For example, the dimensions of some of the elements in the figures may be exaggerated relative to other elements to help improve understanding of embodiments of the present disclosure. The same reference numerals in different figures denote the same elements.

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Furthermore, the terms "include," and "have," and any variations thereof, are intended to cover a non-exclusive inclusion, such that a process, method, system, article, device, or apparatus that comprises a list of elements is not necessarily limited to those elements, but may include other elements not expressly listed or inherent to such process, method, system, article, device, or apparatus.

The terms "couple," "coupled," "couples," "coupling," and the like should be broadly understood and refer to connecting two or more elements mechanically and/or otherwise. The absence of the word "removably," "removable," and the like near the word "coupled," and the like does not mean that the coupling, etc. in question is or is not removable.

As defined herein, "approximately" can, in some embodiments, mean within plus or minus ten percent of the stated value. In other embodiments, "approximately" can mean within plus or minus five percent of the stated value. In further embodiments, "approximately" can mean within plus or minus three percent of the stated value. In yet other embodiments, "approximately" can mean within plus or minus one percent of the stated value.

DETAILED DESCRIPTION OF THE PREFERRED EMBODIMENTS

The following description of the preferred embodiment(s) is merely exemplary in nature and is in no way intended to limit the invention, its application, or uses.

Figure 1:
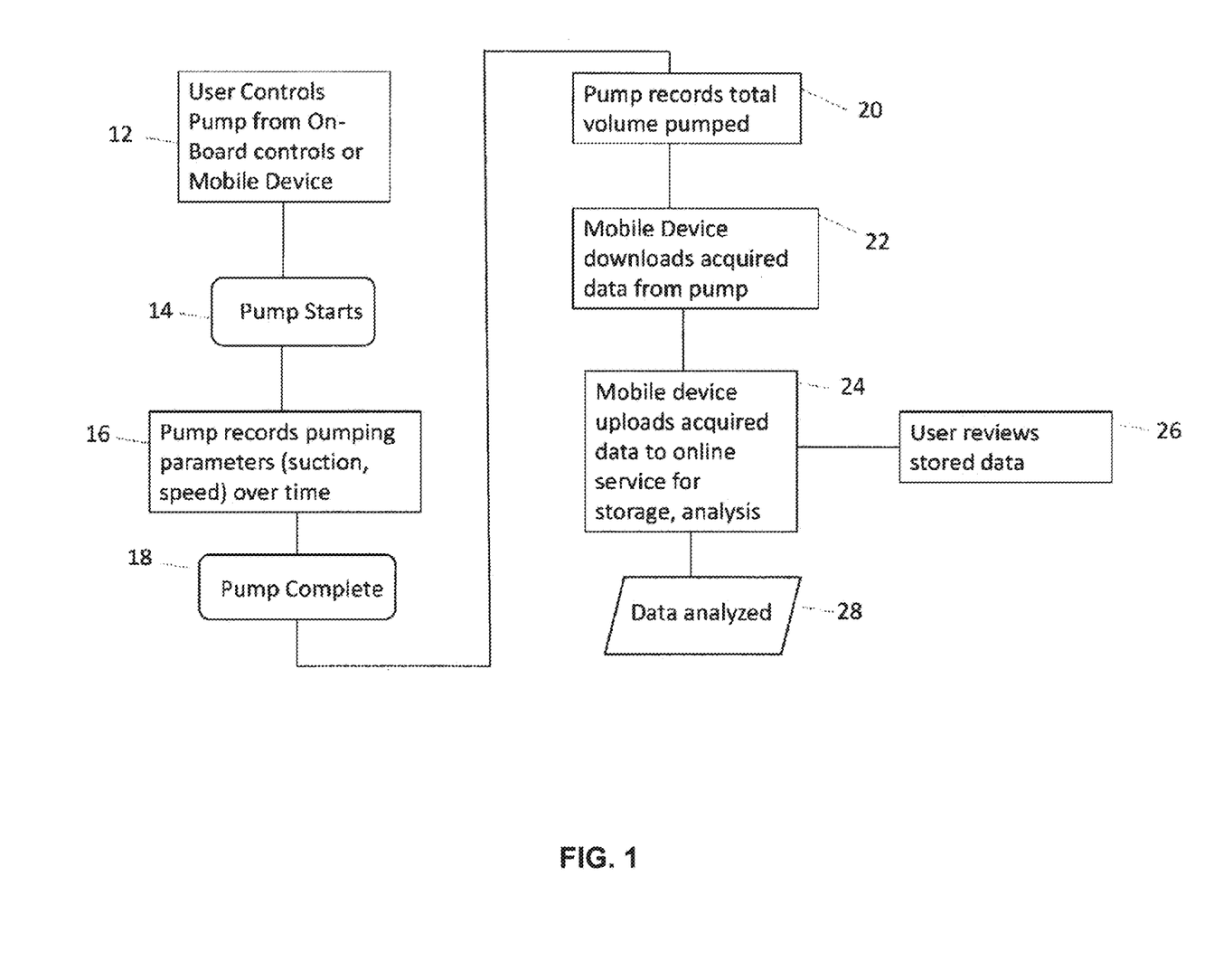
FIG. 1 is a flow diagram of the present breast pump system being used.

The flow diagram of FIG. 1 shows step 12 as controlling the breast pump system by use of a mobile devices, such as iPads or smart phones, or by controls on the device itself. In step 14, the pump starts pumping, and in step 16, pump parameters, such as the amount of suction produced and the speed of pumping is recorded. In step 18, the pumping is competed and stopped. In step 20, the pump system records the total volume of milk pumped and stored. In step 22, the mobile device downloads data from the pump. In step 24, the mobile device uploads the data to an online service that stores and analyses the data. In step 26, the breast pump user can review the data that is stored, or in step 28 the data that has been uploaded is analyzed.

Figure 2:
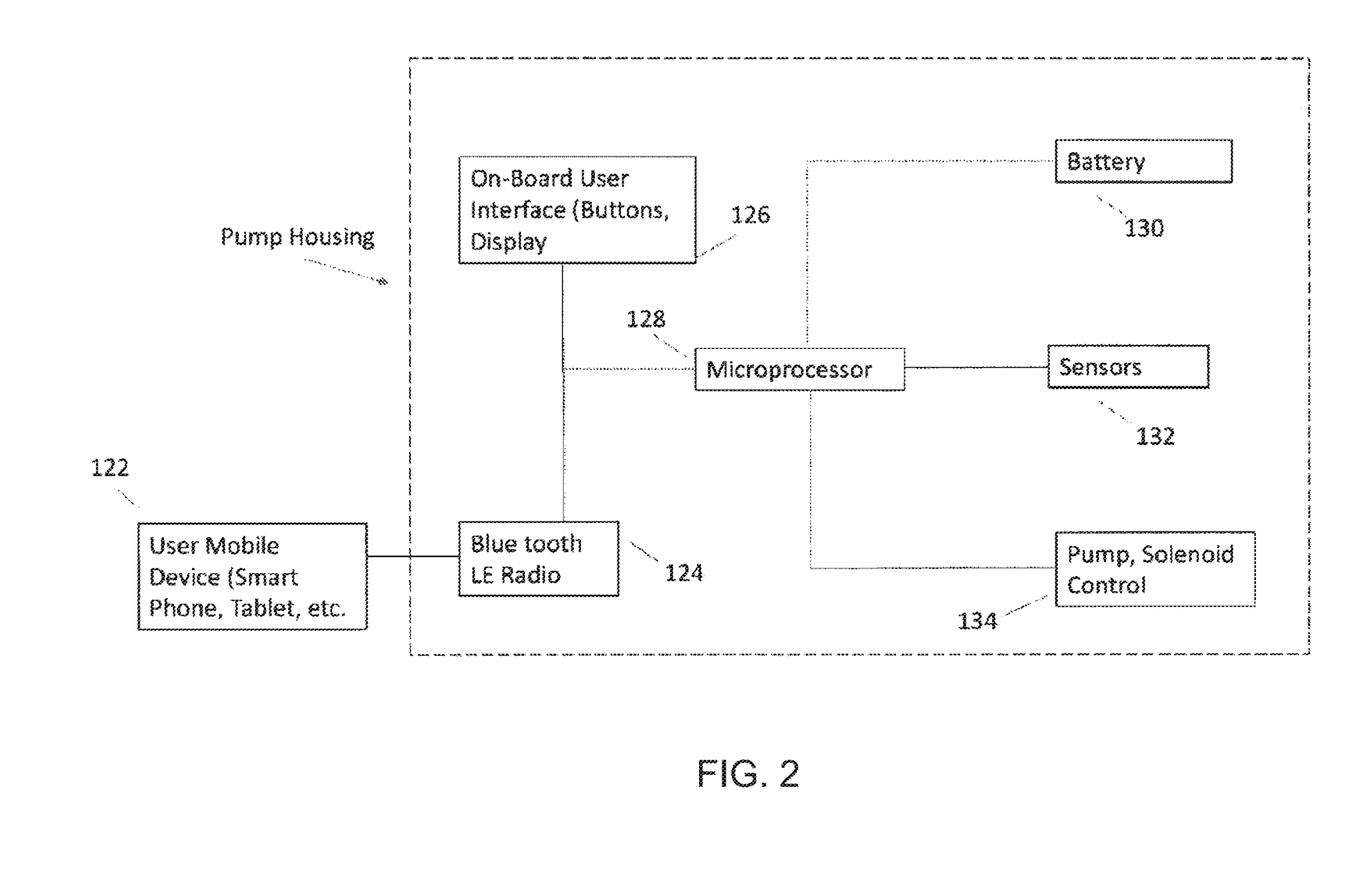
FIG. 2 is a block diagram of an embodiment of the present breast pump system.

The block diagram of FIG. 2 is an embodiment of the present breast pump system. In the pump housing is the on-board user interface 126 which is connected to the microprocessor 128 and a Bluetooth LE radio. Also connected to the microprocessor is the battery 130 power supply, the sensors 132 and the pump and solenoid valve control 134.

Figure 3:
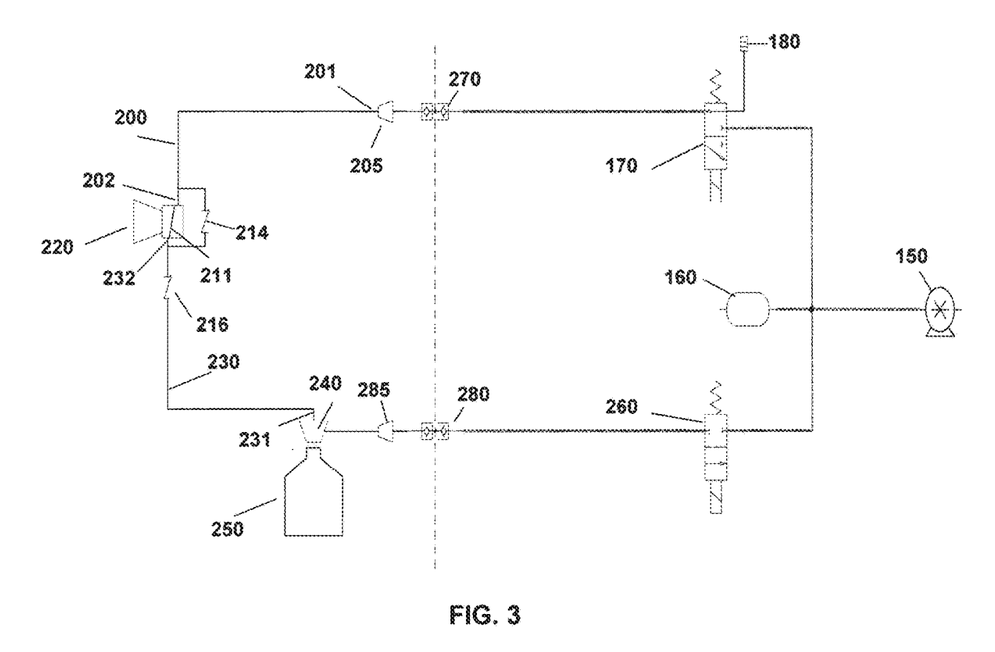
FIG. 3 is a schematic of an embodiment of the present breast pump system.

In the diagram of FIG. 3, an embodiment of the breast pump system 100 has a vacuum pump 150 attached to a power source and a microprocessor (not shown). Fluidly attached to the suction of the pump 150 is a vacuum receiver 160. Fluidly attached to the vacuum receiver is a vent valve 170. In a preferred embodiment, the vent valve is an electrically-operated solenoid valve controlled by a microcontroller (not shown). The vent valve 170 can be a 3-way vent valve or a 2-way vent valve with a check valve. Also attached to the vent valve 170 is a vent 180 with an optional silencer.

The vent valve 170 is configured to fluidly connect to suction tubing 200 having a first end 201 and a second end 202. The first end 201 is coupled to one or more main suction connectors 270 further coupled to the vent valve 170. In some embodiments, the one or more main suction connectors 270 further comprise a self-sealing filter 205.

As is shown in FIG. 3, the second end 202 is fluidly attached to suction port (as described more fully herein) that is further coupled to a breast shield 220. In some embodiments, the suction port is further coupled to an equalization check valve 214. For example, the valve 214 may alternately open and close to prevent fluid flow in one direction (downward from the suction port) while allowing full fluid flow of air in the opposite direction (upward, from pump 150).

In some embodiments, breast shield 220 comprises a suction port and a breast milk port. The two ports exist to enforce the separation between the milk that flows into the milk tubing and the air flow from the suction tubing. The suction tubing 200 attaches to a suction port, and a milk tubing 230 attaches to a breast milk port. Suction pulls the milk down to be collected at the bottom of the breast shield where it flows through the milk tubing 230 to the milk bottle 250. A diaphragm 211 may be in place within the breast shield in order to ensure that no milk reaches the suction port of the breast shield.

The breast shield 220 is further configured for coupling to milk tubing 230. The milk tubing has a first end 231 and a second end 232. The second end 232 fluidly couples to the breast milk port of the breast shield 220. In some embodiments, the breast shield 220 has a milk check valve 216 to block flow of the suction to the milk tubing 230 and prevent milk from backflowing from the milk tubing to the breast shield. In one embodiment, this milk check valve is a combination duckbill-umbrella valve that comprises the milk check valve 216 and the equalization check valve 214.

The first end of the milk tubing 231 is configured to couple to a milk bottle 250 with an optional lid 240. Positioned between the milk bottle and the vacuum pump 150 is an isolation/bottle valve 260, which maintains vacuum in the milk bottle. In one embodiment, the bottle valve is an electrically-operated solenoid valve under the control of a microcontroller (not shown).

Optionally, the suction tubing 200 and the milk tubing 230 can each have removable connectors 270 and 280, respectively. This allows the breast shield 220 and the milk bottle 250 to be disconnected from the rest of the device for cleaning. In some embodiments, the remainder of the device 100 that is disconnected is enclosed in a pump housing (not shown) for convenience. In some embodiments, the suction tubing 200 and milk tubing 230 can be attached together such as by thermal bonding to act as a single assembly for convenience to the user.

Further optionally, a second breast shield (not shown) can be fluidly attached to the system at additional connectors 270 and 280, so that both breasts can be pumped at the same time.

Figure 4:
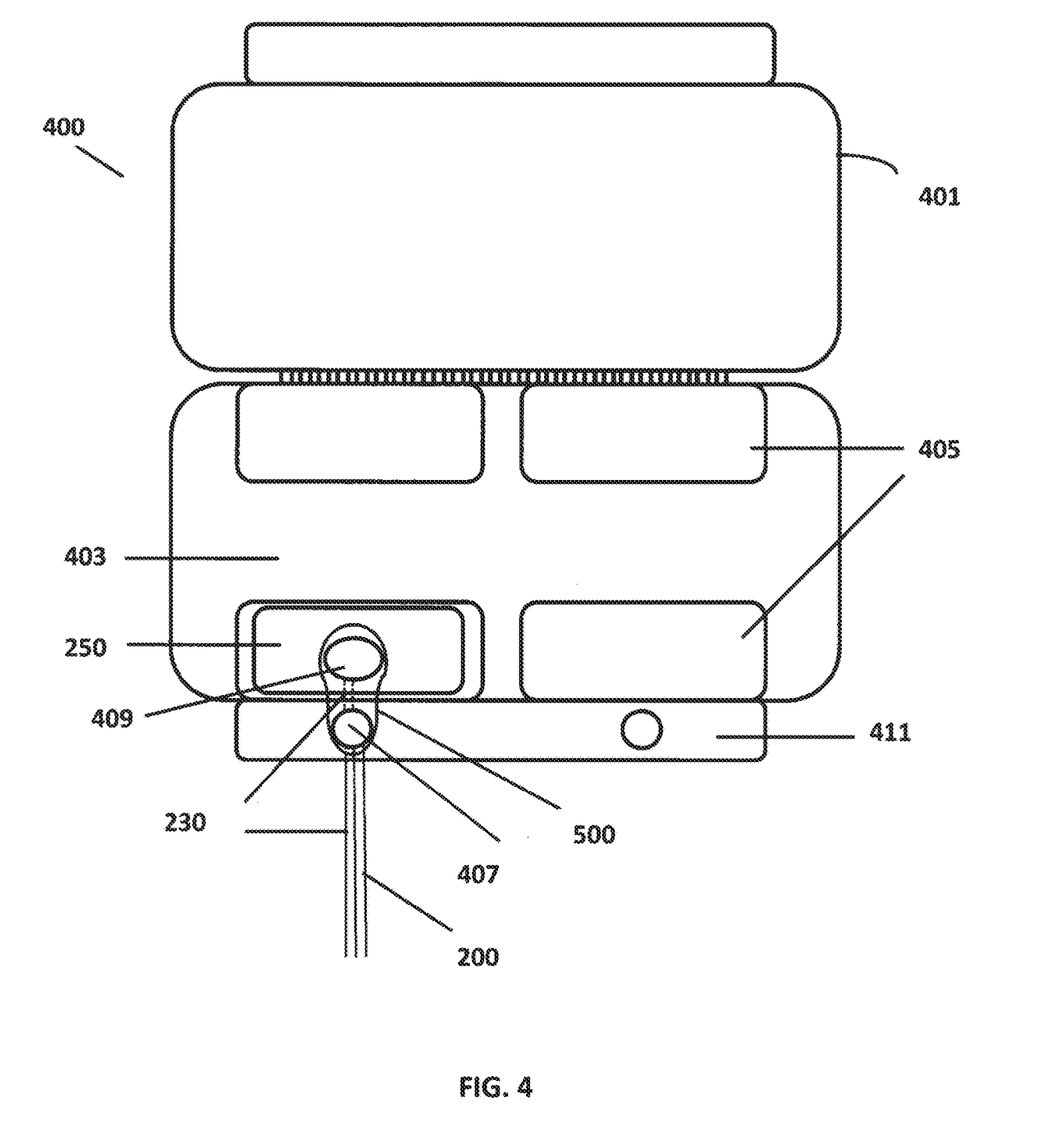
FIG. 4 is an illustration of an exemplary embodiment of an enclosure for a breast pump system.

In other embodiments, and with exemplary reference to FIG. 4, a breast pump enclosure 400 is provided that comprises a main compartment 403 and a lid 401. In some embodiments, main compartment 403 comprises one or more openings 405 for holding bottles 250, as well as a general opening portion for storing ice packs, etc. Enclosure 400 can also include a suction connection portion 411 that contains the coupling ports 270 and 280.

Enclosure 400 can also include a pump housing (not shown) for housing one or more aspects of system 100. For example, enclosure 400 can house vacuum pump 150, microprocessor 290, and vacuum cylinder 160, in an internal compartment within enclosure 400. In some embodiments, enclosure 400 and/or the internal compartment is constructed of a water-resistant material to minimize damage to microprocessor 290, should a liquid (such as milk or water), come into contact with a portion of enclosure 400. In other embodiments, enclosure 400 is comprised of an insulation material to maintain the temperature of the milk bottles and the internal temperature of the enclosure.

In some embodiments, enclosure 400 has one or more compartments (not shown) for removably containing various features of system 100. For example, in some embodiments, enclosure 400 has one or more compartments for removably containing tubing 200 and 230, as well as the connectors 270 and 280 that may be attached thereto, and one or more breast shields 220.

In one embodiment, enclosure 400 is configured such that at least one bottle opening 405 is adjacent to the 3-way vent solenoid 170, such that a dual connector 500 can be fluidly connected to both the 3-way vent solenoid 170 and bottle 250. For example, with reference to FIGS. 4, 5A and 5B, in some embodiments, dual connector 500 comprises both suction connector 270 and milk connector 280 in one integrated piece. That is, the dual connector 500 contains a milk bottle connector portion 409 and a suction connector portion 407. The milk bottle connector portion 409 is configured to couple fluidly to the top portion of a bottle 250. The suction connector portion 407 is configured to sealingly couple to the filter cartridge 700 and filter insert 605 portion of the suction connection portion 411 of the enclosure (which are described in more detail, herein).

Figure 5A:
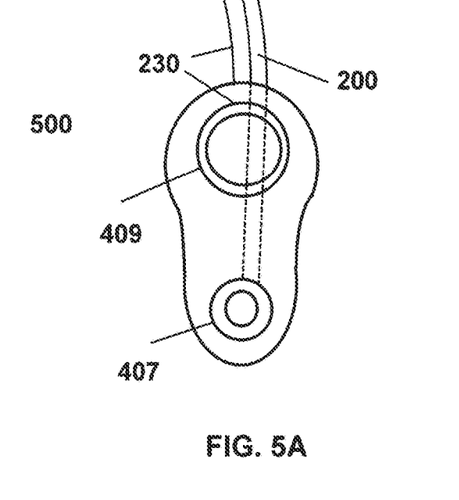
FIG. 5A is an illustration of an exemplary embodiment of a dual bottle/pump connector.
Figure 5B:
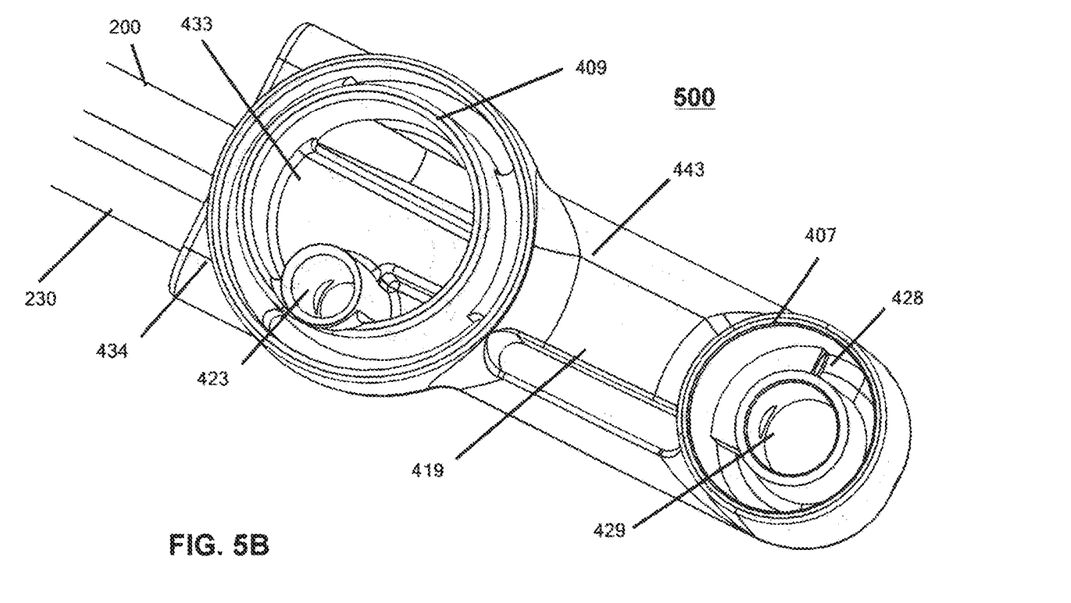
FIG. 5B is an illustration of an exemplary embodiment of a dual bottle/pump connector.

In one embodiment, dual connector 500 is fluidly connected to both suction tubing 200 and milk tubing 230. In other embodiments, suction tubing 200 and milk tubing 230 are adhered together or enclosed together such that the two sets of tubing resemble a single tube. In those embodiments, dual connector 500 has a single port for fluidly connecting to the adjoined suction tubing 200 and milk tubing 230.

With reference to FIG. 5B, dual connector 500 mates to suction tubing 200 at suction port 433 and to milk tubing at milk port 434. Dual connector 500 seals to the bottle 250 on connector portion 409, optionally via lid 240. Dual connector 500 seals to filter (not shown) via connector portion 407. Milk flows from milk tube 230 through milk port 434 and into the bottle via milk transfer port 423. Bottle suction to facilitate the transfer of milk down the milk tube is coupled to the bottle from filter through bottle suction entry 428 via internal path 443. Main suction is coupled to suction tube 200 from filter through main suction entry 429 via internal path 419 and further via suction port 433.

Figure 6A:
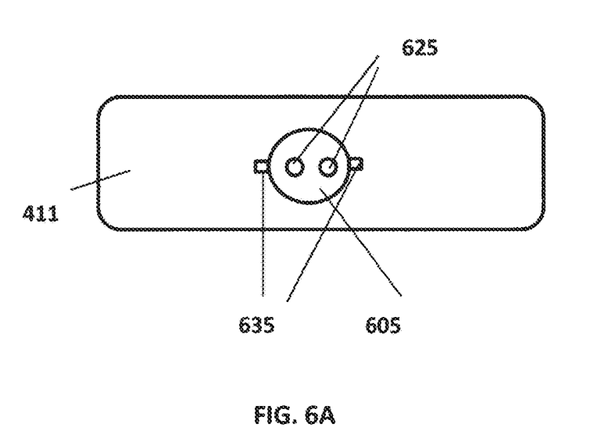
FIG. 6A is an illustration of an exemplary embodiment of a filter portion of an enclosure.
Figure 7:
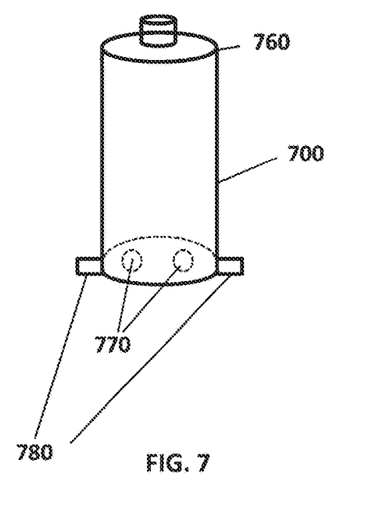
FIG. 7 is an illustration of an exemplary embodiment of a filter cartridge for use in a breast pump system.

With reference to FIGS. 6A and 7, embodiments of the suction connection portion 411 of enclosure 400 are shown. Suction connection portion 411 comprises a filter insert 605 configured to receive a filter cartridge 700. Filter cartridge 700 is contained within a plastic or polypropylene housing. The filter cartridge allows air to flow from the vacuum pump side towards an outlet side, and collects any milk, bacteria, or particulates that might otherwise migrate into the vacuum pump. Filter cartridge 700 is disposable and can be regularly replaced when necessary. Filter insert 605 can have one or more vent holes 625 for directing air from the pump toward the suction tubing 200 and/or milk tubing 230. Similarly, filter cartridge 700 can have one or more corresponding vent holes 770, such that when the filter cartridge 700 is inserted into filter insert 605, air can pass freely from the pump through filter cartridge 700 and out through atop end 760 of filter. The top end 760 of the filter can also comprise one or more air vents that are sized to correspond with suction connector portion 407 of the dual connector 500.

In some embodiments, filter cartridge 700 has one or more legs 780 that are used to align the filter cartridge 700 with the filter insert 605 and for securing the filter cartridge 700 into the filter insert 605. For example, in some embodiments, the legs 780 can be used to align with the open portions 635 of filter insert 605. Once the filter cartridge 700 is inserted into the insert 605, the filter can be twisted into a locking position, wherein the legs 780 are moved to a position out of alignment with the open portions 635 of the filter insert.

Figure 6B:
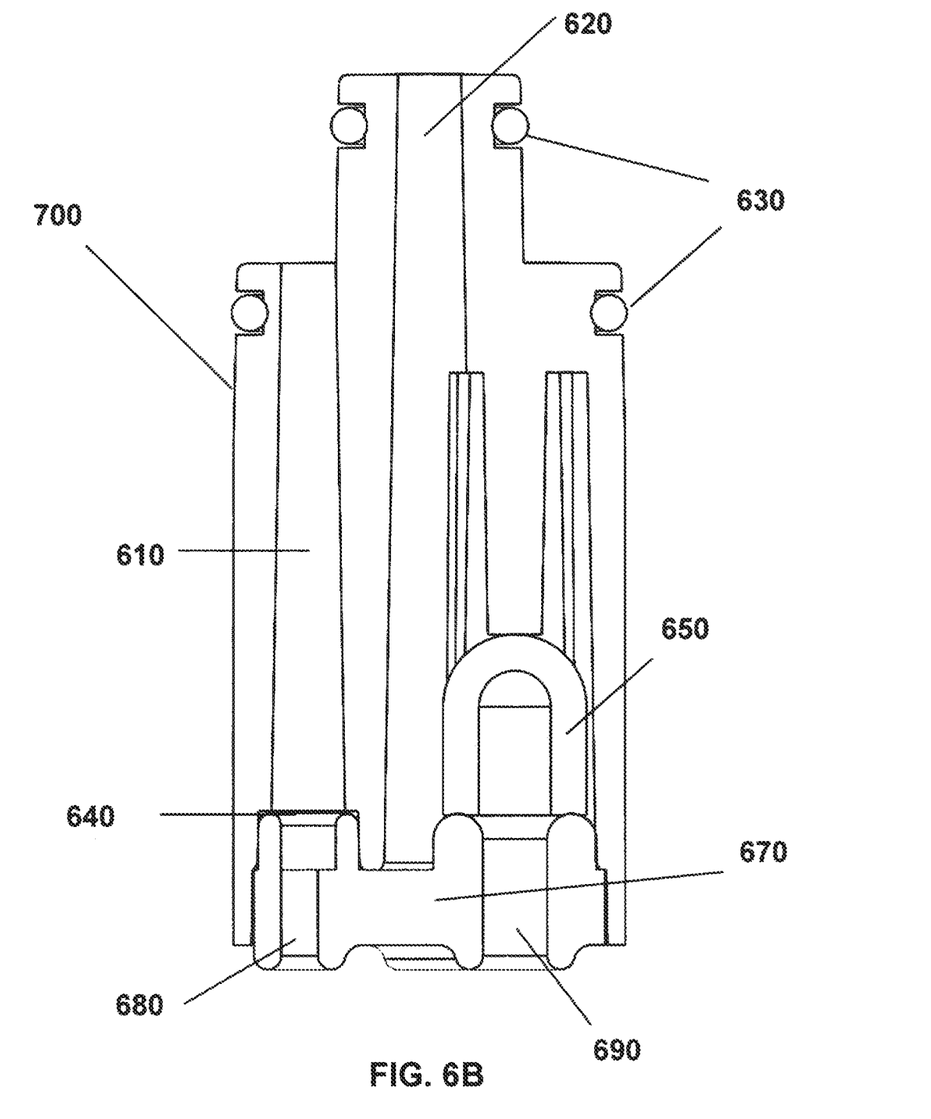
FIG. 6B is an illustration of an exemplary embodiment of a filter cartridge.

With reference to FIG. 6B, in some embodiments, filter cartridge 700 is configured such that there is an internal bottle suction path 610 and an internal main suction path 620. That is, vent holes 680 correspond to bottle suction path 610, and vent holes 690 correspond to main suction path 620. The dual suction paths allow a single filter housing to protect both the main suction and the bottle suction portion of the internal pneumatic system. In some embodiments, filter cartridge 700 contains one or more o-rings 630 to facilitate sealing the filter to the connector 407. In addition, in some embodiments, filter cartridge 700 comprises a filter element 640 to filter bacteria and minimize liquid from entering the pump housing. In some embodiments, filter 640 serves to minimize bacterial contamination of the main pump unit, either from aerosolized bacteria in the air coming out of the milk bottle or from accidental overflow of liquid milk into the filter. In one embodiment, filter 640 is a 0.45 micron polytetrafluoroethylene (PTFE) membrane. The pore size minimizes aerosolized bacteria penetration and the hydrophobic nature prevents liquid from entering. The membrane may optionally include an oleophobic coating to improve performance with milk that has a low surface tension.

Filter cartridge 700 can additionally comprise a filter element 650 to provide additional protection from liquid ingress on the main suction path. In some embodiments, the sealing filter 650 can be a self-sealing filter. In the event of liquid ingress to the suction tubing, the filter 650 will stop liquid from entering the pump 150 inside the enclosure since filter 650 will seal upon exposure to excess moisture. One embodiment of the self-sealing filter 650 would be an air-permeable polymer bead matrix in which some beads are made of carboxyl methylcellulose or other material that swells when exposed to liquid. When the material swells, it would seal the matrix such that no further air or liquid could penetrate. In some embodiments, filter cartridge 700 comprises an elastomeric member 670 to facilitate sealing filter 700 within insert 605.

Figure 6C:
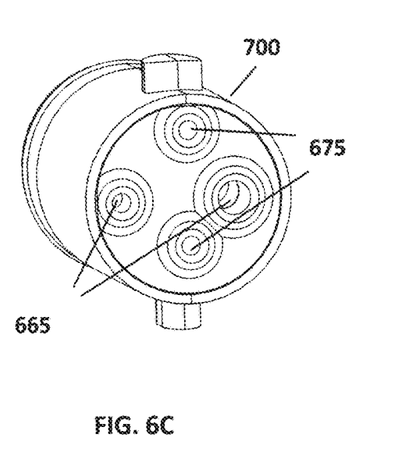
FIG. 6C is an illustration of an exemplary embodiment of a filter cartridge.

With regards to FIG. 6C, filter cartridge 700 additionally may have two positions in the filter insert 605. One is "open" 665 where the vent holes 770 are aligned with their respective suction ports 625. The other is "closed" 675 where a portion of the bottom of the filter cartridge aligns with the ports 625 on the enclosure and plugs them, the purpose being so that the user can single pump only one side, but the pneumatic integrity of the system will be maintained.

As should be appreciated, the filter cartridge 700 can be used in a myriad of applications, in addition to or alternatively to use in a breast pump. Because of the dual suction paths and filter system, the filter cartridge 700 facilitates separation of suction streams and provides for minimization of contaminants (including bacteria, liquids, and the like). While embodiments of the filter cartridge 700 are described herein with respect to a breast pump, the filter cartridge 700 should not be limited to this type of application.

Figure 8:
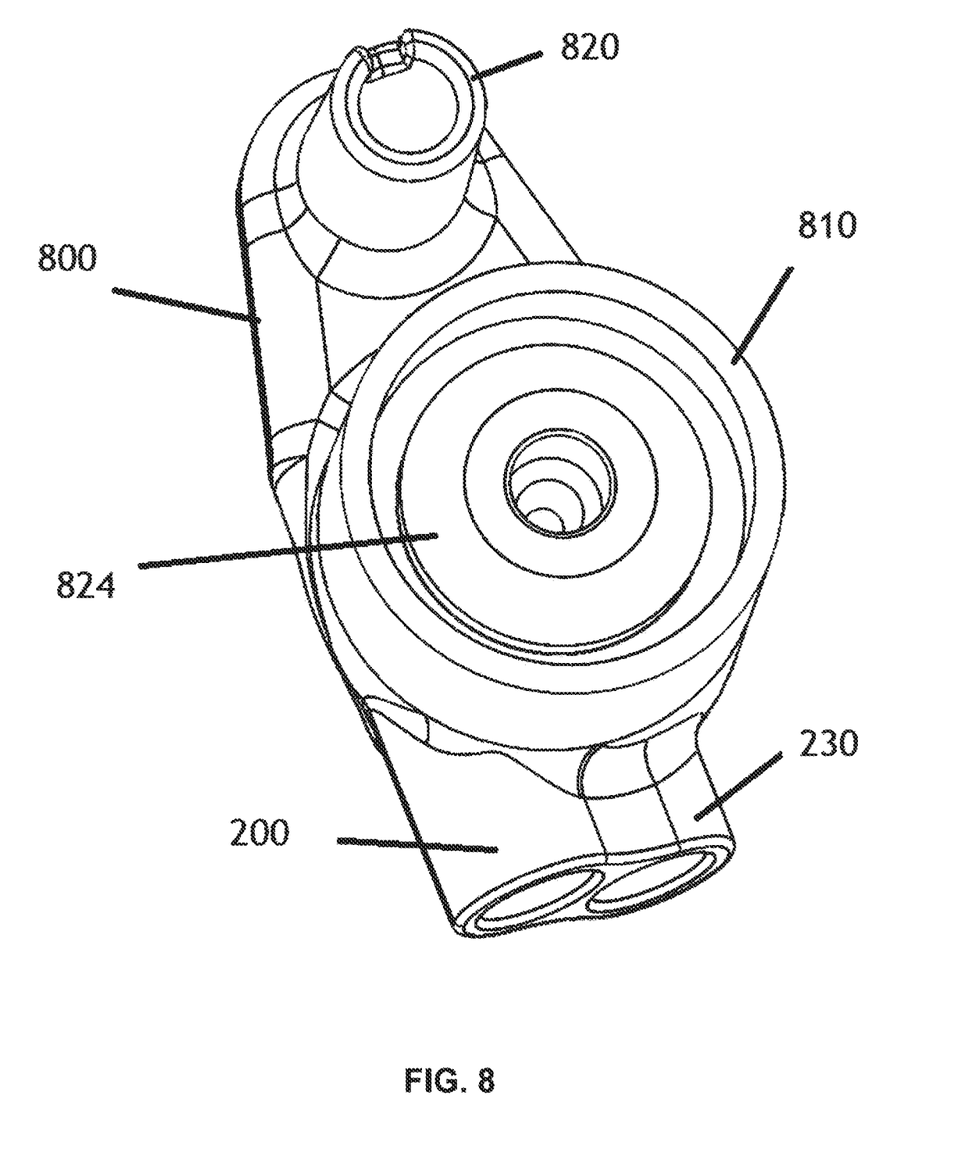
FIG. 8 is an illustration of an exemplary embodiment of a dual breast shield/suction connector.
Figure 9A:
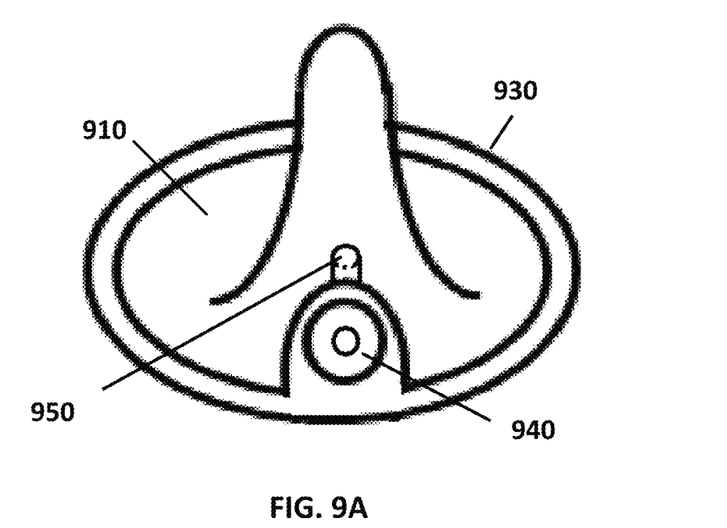
FIG. 9A is a first schematic of an embodiment of a breast shield diaphragm part.
Figure 9B:
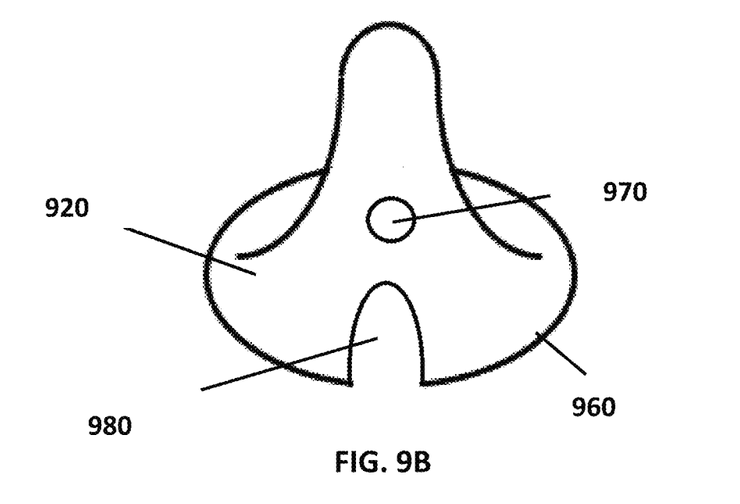
FIG. 9B is a second schematic of an embodiment of a breast shield cover.
Figure 9C:
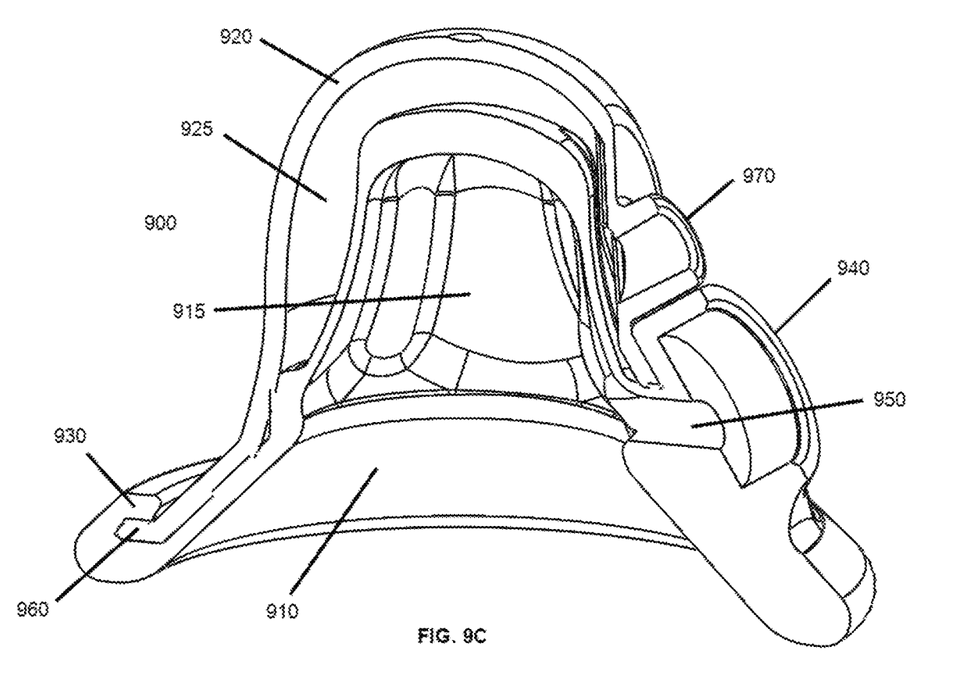
FIG. 9C is a section view of an embodiment of a breast shield with both the diaphragm and the cover.

In some embodiments, and with reference to FIGS. 8 and 9A-C, the suction and milk separator device can be configured as a cover portion 920 of a breast shield 900. With reference to FIGS. 9A-C, embodiments of an integrated breast shield 900 are shown. Breast shield 900 comprises a soft inner part or diaphragm 910 and a cover 920. Diaphragm 910 is made of a soft silicone rubber or plastic polymer and is designed to stimulate the nipple in a manner similar to a baby's mouth and tongue.

Diaphragm 910 is comprised of a flexible material and shaped to reasonably conform to a user's nipple. Diaphragm 910 interfaces sealingly with the cover 920. In some embodiments, diaphragm 910 comprises an outer lip 930 that interfaces with cover inner lip 960. Milk from a user's breast travels through milk collection outlet 950 in diaphragm 910 through a milk collecting port 940, which is fluidly connected to milk tubing 230 through a milk tubing connector port 810.

In some embodiments, the breast shield 900 generates suction at the user's nipple by applying suction from the suction tubing 200 to the back side of diaphragm 910. In turn, that suction causes diaphragm 910 to elongate into the cover 920. This displacement in turn generates suction at the user's breast, with the benefit that the suction on that "wet side" of diaphragm 910 (i.e., the side adjacent to the user's nipple where milk is expelled) is isolated from the "dry side" where the tubing connects. As such, the suction portion of the system 100 is closed to reduce any contamination from milk or bacteria into the pump 150.

An exemplary integrated connector 800 is illustrated in FIG. 8 that comprises the milk tubing connector 810, which fluidly couples to both milk tubing 230 and the breast milk collecting port 940 of the breast shield 900. Connector 800 additionally can comprise a suction tubing connector 820, which fluidly couples to both suction tubing 200 and a suction port 970 of the breast shield.

The milk tubing connector 810 is configured to hold a milk separator diaphragm or check valve 824.

The shape of milk collecting port 940 conforms to the shape of milk tubing connector 810, such that there is a fluid connection between the two that prevents milk from leaking out.

Cover 920 is shaped to fit onto the diaphragm part 910. The edge 960 of cover 920 is configured to sealingly interface with the lip 930 of diaphragm 910, such that outside air does not enter into the area between diaphragm part 910 and cover 920, except from suction tubing 200. Cover 920 has a port 970 that is configured to fluidly couple to suction tubing connector 820.

For example, in some embodiments, suction tubing connector 820 is fluidly coupled to suction tubing 200 and provides suction to the breast shield 900. The cover 920 further comprises an interface port 980 that is used to affix the cover 920 onto the diaphragm part 910. For example, with respect to FIG. 9C, the interface port 980 aligns with the top of outlet 940 and is affixed onto outlet 940. The edge 960 of the cover 920 slides under lip 930 of diaphragm 910 and is removably sealed thereunder. In some embodiments, once cover 920 and diaphragm 910 are aligned, connector 800 is fluidly connected to the breast shield 900. That is, the milk tubing connector 810 fluidly couples to the breast milk collecting port 940 of the breast shield 900 and the suction tubing connector 820 fluidly couples to the suction port 970 of the breast shield.

During operation, the diaphragm 910 is pressed to the user's nipple such that it interfaces sealingly with the user's nipple and creates a wet side space 915 between the user's nipple and the diaphragm 910. The breast cover 920 interfaces sealingly with diaphragm 910 to create a dry side space 925 between the diaphragm and the cover to transfer suction to the user's nipple and to direct the flow of expressed milk away from the breast to the suction and milk collection outlet 950. When excess milk suction is applied to the breast shield via milk tubing 230, suction can build up on the wet side 915 such that the air pressure is lower than what is otherwise applied to the dry side 925 via the suction tubing 200. When the air pressure on the wet side 915 is lower than the pressure on the dry side 925, the diaphragm 910 may collapse towards the user's nipple, causing additional beneficial stimulation. This excess vacuum may need to be relieved by venting to an area of higher pressure. In some embodiments, an equalization check valve may be used to relieve excess pressure on the wet side 915 by allowing venting to ambient air outside the breast shield or by venting to dry side 925. In one embodiment, check valve 824 may comprise the equalization check valve such that the equalization check valve allows air from the dry side 925 to pass to the wet side 915 when the main suction tubing 200 is at a pressure higher than pressure at the nipple.

In some embodiments, breast cover 920 is sized and shaped to resemble a human breast. That is, in some embodiments, the breast cover has a rounded shape, such that when the breast shield system (breast cover 920 interfaced with the diaphragm 910) is affixed to a breast, the profile resembles the rounded, natural shape of a breast. When in use, the breast shield system can fit discreetly inside a bra. In other embodiments, the breast shield system can fit discreetly within a removable bra pad during use.

The use of a vacuum cylinder allows the use of a smaller, quieter pump than would otherwise be required. The pressure vessel acts as a vacuum storage reservoir. As the pump stays running throughout the cycle, the vent solenoid opens to the manifold and the pump, and closes the vent, and provides vacuum for the system. When the vent solenoid closes to the pump and the opens to the vent and the manifold, the system is vented, except for the pressure vessel, which is being further vacuumed by the continuously running pump. When the vent solenoid is closed to the vent and open to the manifold and pump, the lower pressure in the pressure vessel provides a vacuum boost to the system, even with a smaller, quieter pump, and the pump runs continuously rather than switching on and off.

The present breast pump system can be controlled wirelessly by an app on a user's smart phone or other digital device or by a front-panel display and controls. The remote app gives users the option of having very detailed control of the settings (pumping curves, detailed cycle timings, etc.), or allows simple single-slider-based control of the settings. Further, the pump system captures the detail of the volume of milk produced in a given pumping session. This data is uploaded from the app to an interne cloud service for storage, analysis and retrieval to display. The app also may track pumping duration, breastfeeding frequency and diaper changes, so multiple apps or devices are not needed.

Figure 10:
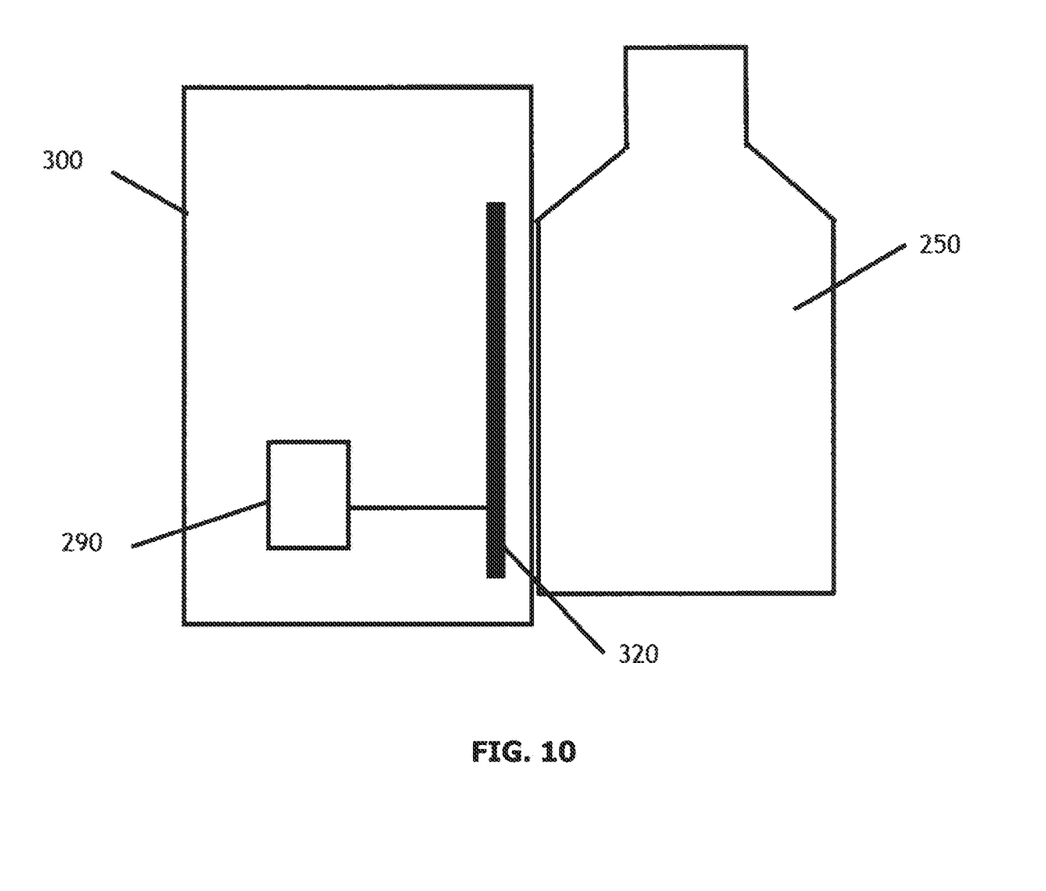
FIG. 10 is a diagram of a level sensor with the milk bottle of the present invention.

As shown in FIG. 10, a milk level sensor 320 can be used to determine the volume of milk pumped. As shown in FIG. 10, the sensor 320 is positioned inside the pump housing 310, running the height of the milk bottle. The bottle is secured so that the air gap between the bottle and the sensor is minimized. The sensor electrodes are parallel to and facing the bottle. In a preferred embodiment, there is one senor per bottle and one bottle per breast so as to be able to track milk expression independent per breast.

An example of a preferred sensor is disclosed in US 2016/0,003,663A1, which is hereby incorporated by reference.

The microprocessor 290 is able to calculate the volume of milk expressed. In a preferred embodiment, the sensor 320 can be paired with a load cell to measure the weight of the milk expressed in order to calculate the density of the milk, yielding information about the solids content of the milk.

The pump system 100 can have custom settings entered by the user. Optional presets are provided that may be helpful to the new user. This provides new moms with a better starting point, rather than just being given a pump and told to start pumping with no other guidance. The pump is much quieter than those currently used, because a much smaller pump can be used. In a preferred embodiment, a brushless motor, rather than using a traditional diaphragm pump, is used. In another preferred embodiment, a linear pump motor that is inherently quieter is used. In another preferred embodiment, a vacuum cylinder to boost the suction is used with a pump, allowing the pump to run continually, thereby allowing a smaller (and therefore quieter) motor to be used on the pump, rather than the pump being turned on and off. The present breast pump system has the collection bottle and the pump fluidly and remotely connected to the breast shield by lengths of tubing. In a preferred embodiment, clothing and undergarments cover and engage with the shield and tubing. This provides a discreet system that can be worn under a woman's shirt.

Figure 11A:
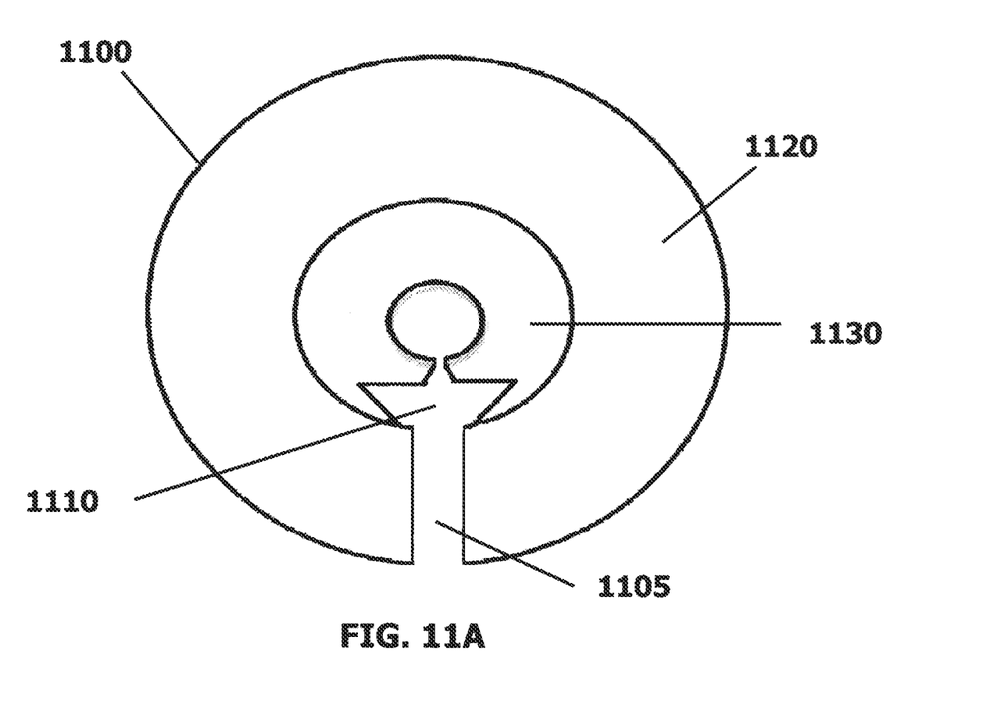
FIG. 11A is an illustration of an exemplary embodiment of a breast pad.
Figure 11B:
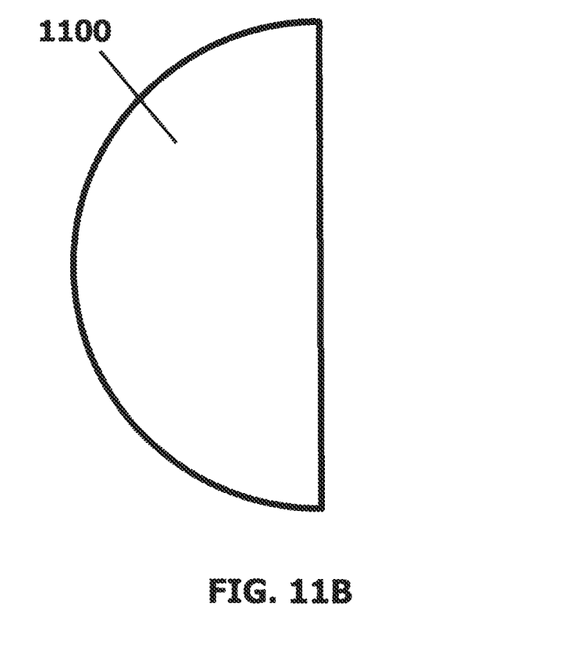
FIG. 11B is an illustration of an exemplary embodiment of a breast pad.

As shown in FIGS. 11A and B, this improved product offers discretion in that women will not have to remove their shirts when breast pumping. In a preferred embodiment, a removable bra pad 1100 may be used to hold the breast shields in place and to prevent leaking milk from showing. These breast pads also serve as the lining of the bra. The removable cups will allow this bra to seamlessly go from a pumping bra to a nursing bra. As illustrated in an exemplary embodiment in FIG. 11B, the side profile of the breast pad conforms to the shape of a breast.

In exemplary embodiments and with reference to FIG. 11A, an interior 1120 of bra pad 1100 comprises a central cavity 1130 for receiving a breast shield 900. The interior 1120 of bra pad 1100 further comprises a milk connector cavity 1110 and adjacent tubing pathway 1105. When connector 800 is coupled to breast shield 900, the breast shield 900 is configured to fit within bra pad 1100 such that the attached connector 800 fits within the milk connector cavity 1110 and the attached milk collection and suction tubing fits within the tubing pathway 1105.

Milk tubing 230 and/or suction tubing 200 are removable for easy cleaning. During use, the tubes (or conjoined tube) dangle down the torso of the user. In some embodiments, one set of tubes will connect to the milk collection bottle, and the other set will connect to the vacuum pump. In other embodiments where the tubes are attached together, the tubes dually connect to both the milk connection bottle and vacuum pump, as shown and described with respect to FIG. 4. Similarly, in some embodiments where the tubes are attached together, the tubes dually connect to the breast cover and breast nipple, as shown and described in FIGS. 8 and 9A-C. From the side, the bra consists of multiple pieces that are hidden in the cup of the bra. Those pieces include, bra pad 1100, connector 800, tubing 230 and 200, and breast shield 900.

The embodiments were chosen and described to best explain the principles of the invention and its practical application to persons who are skilled in the art. As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed:

1. A breast shield system comprising:
a suction port coupled to a suction portion of a connector;
a breast shield configured with a soft flexible inner portion having a milk collection port coupled to a milk collection portion of the connector, wherein the milk collection portion of the connector is further coupled to a milk tubing, and
wherein the milk tubing is of a sufficient length such that it couples to a collection bottle that is remote from the breast shield;
wherein the soft flexible inner portion has a closed distal end with the milk collection port arranged proximally from the closed distal end;
wherein the breast shield is further configured with a cover portion, the cover portion located in immediate proximity to the soft flexible inner portion such that the cover and inner portions interface sealingly together; and
wherein the suction port and milk collection port are disposed adjacent to one another.

2. The breast shield system of claim 1, wherein the cover portion has a profile sized and shaped to resemble a breast.

3. a bra pad conforming in shape to the breast shield and removably coupled to an outer portion of the cover portion, wherein the bra pad has a first side with an indented profile that removably couples to the outer portion of the cover potion, and the bra pad has a second side that can be inserted into a bra to secure and hide the breast shield.

4. The breast shield system of claim 1, wherein the suction portion and milk collection portion of the connector are separated from one another.

5. The breast shield system of claim 1, wherein the suction port is configured for one of removable or fluid coupling to the suction portion of the connector, and wherein the milk collection port is configured for one of removable or fluid coupling to the milk collection portion of the connector; and wherein the suction portion of the connector is further coupled to a suction tubing.

6. The breast shield system of claim 1, wherein the soft flexible inner portion is configured to receive suction from a suction tubing coupled to the suction portion of the connector and wherein the soft flexible inner portion expands towards the cover portion, thereby generating suction at a user's nipple.

7. The breast shield system of claim 6, wherein the soft flexible inner portion is configured to interface sealingly to a user's breast.

8. The breast shield system of claim 1, wherein the soft flexible inner portion is configured to receive suction from a suction tubing coupled to the suction portion of the connector and expand towards the cover portion, thereby generating suction at a user's nipple, and further isolating a first side adjacent to the user's nipple from a second side adjacent to an interior portion of the cover portion of the breast shield system.

9. The breast shield system of claim 1, wherein the soft flexible inner portion is configured to receive suction from a suction tubing coupled to the suction portion of the connector and negative pressure from the milk tubing and expand towards the cover portion, and wherein the soft flexible inner portion is configured to collapse towards a user's nipple when the air pressure on a first side adjacent to the user's nipple is lower than the air pressure on a second side adjacent to an interior portion of the cover portion of the breast shield system.

10. The breast shield system of claim 9, further comprising an equalization check valve to relieve excess negative pressure on the first side by allowing venting to ambient air outside the breast shield system.

11. A breast shield system comprising:

a suction port coupled to a suction portion of a connector;

a breast shield configured with a soft flexible inner portion having a milk collection port coupled to a milk collection portion of the connector, and wherein the milk collection portion of the connector is further coupled to a milk tubing, and wherein the milk tubing is of a sufficient length such that it couples to a collection bottle that is remote from the breast shield;

wherein the breast shield is further configured with a cover portion, the cover portion located in immediate proximity to the soft flexible inner portion such that the cover and inner portions interface sealingly together, and wherein the soft flexible inner portion is configured to receive suction from a suction tubing coupled to the suction portion of the connector and negative pressure from the milk tubing and expand towards the cover portion, and wherein the soft flexible inner portion is configured to collapse towards a user's nipple when the air pressure on a first side adjacent to the user's nipple is lower than the air pressure on a second side adjacent to an interior portion of the cover portion of the breast shield system; and wherein the connector further comprises an equalization check valve to relieve excess negative pressure on the first side by allowing venting to the second side of the breast shield system.

* * * * *